US006461810B1

(12) United States Patent
Fresco et al.

(10) Patent No.: US 6,461,810 B1
(45) Date of Patent: Oct. 8, 2002

(54) TRIPLEX IN-SITU HYBRIDIZATION

(75) Inventors: Jacques R. Fresco, Princeton, NJ (US); Marion D. Johnson, East Windsor, NJ (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/531,000

(22) PCT Filed: Nov. 10, 1998

(86) PCT No.: PCT/US98/23765
§ 371 (c)(1),
(2), (4) Date: Sep. 8, 2000

(87) PCT Pub. No.: WO99/24622
PCT Pub. Date: May 20, 1999

Related U.S. Application Data

(60) Provisional application No. 60/064,997, filed on Nov. 10, 1997.

(51) Int. Cl.$^7$ .............................. C12Q 1/70; C12Q 1/68; G01N 33/48

(52) U.S. Cl. .............................. 435/5; 435/6; 435/40.5; 435/40.51; 536/24.31

(58) Field of Search .............................. 435/5, 6, 40.5, 435/40.51; 536/24.31

(56) References Cited

U.S. PATENT DOCUMENTS 5,422,251 A * 6/1995 Fresco .......................... 435/91.1
5,472,842 A * 12/1995 Stokke et al. ................... 435/6
5,538,869 A * 7/1996 Siciliano ...................... 435/91.2

FOREIGN PATENT DOCUMENTS

WO          WO 96/14009      * 12/1996

OTHER PUBLICATIONS

Best, CG et al., "Energetics of Formation of Sixteen Triple Helical Complexes Which Vary at a Single Position within a Pyrimidine Motif", *J. Am. Chem. Soc.*, 1995, vol. 117, No. 4, pp. 1894–1193.
Felsenfeld, G et al., "Studies on the Formation of Two– and Three–Stranded Polyribonucleotides", *Biochemica Biophysica Acta*, vol. 26, (1957), pp. 457–468.
Fossella, JA et al., "Relative Specificities in Binding of Watson—Crick Base Pairs By Third Strand Residues in a DNA Pyrimidne Triplex Motif", *Nucleic Acids Res.*, 1993, vol. 21, No. 19, pp. 4511–4515.
Fresco, JR et al., "The Accomodation of Noncomplementary Bases In Helical Polyribonucleotides and Deoxyribonucleic Acids", *Proc. Nat. Acad. of Sciences*, 1960, vol. 46, No. 3, pp. 311–321.
Fresco, Jr, "Some Investigations on the Secondary and Tertiary Structur of Ribonucleic Acids", *Informational Macromolecules*, 1963, pp. 121–142.

Gabbay, EJ et al., "Intercalating Agents as Probes of Chromatin Structure", *Methods Cell Biol.*, 1978, Chap. 18, pp. 351–384.
Giovannangeli, C et al., "Accessibility of Nuclear DNA to Triplex–Forming Oligonuleotides: The Integrated HIV–1 Provirus as a Target", *Proc. Natl. Acad. Sci. USA*, 1997, vol. 94, pp. 79–84.
Johnson, M et al., "Third–Strand in Situ Hybridization (TISH) to Non–Denatured Metaphase Spreads and Interphase Nuclei", *Chromosoma*, 1999, pp. 181–189.
Le Doan, T et al., "Sequence–Specific Recognition, Photo Crosslinking and Cleavage of the DNA Double Helix by an Oligo–α–thymidylate Covalently Linked to An Azidopoflavin Derivative", *Nucleic Acids Research*, 1987, vol. 15, pp. 7749–7760.
Letagi, AG et al., "Specificity in Formation of Triple–Stranded Nucleic Acid Helical Complexes: Studies with Agarose–Linked Polynucleotide Affinity Columns", *Biochemistry*, 1988, vol. 27, 9108–9112.
Maher, LJ et al., "Kinetic Analysis of Oligodeoxyribonucleotide–Directed Tirple–Helix Formation on DNA", *Biochemistry*, 1990, vol. 29, pp. 8820–8826.
McShan, WM et al., "Inhibition of Transcription of HIV–1 in Infected Human Cells by Oligodeoxynucleotides Designed to Form DNA Triple Helices", *J. Biol. Chem.*, 1992, vol. 267, pp. 5712–5721.
Moser, He et al., "Sequence–Specific Cleavage of Double Helical DNA by Triple Helix Formation", *Research Articles*, 1987, vol. 238, pp. 645–650.
Pinkel, D et al., "Cytogenic Analysis Using Quantitative, High–Sensitivity, Fluorescence Hybridization", *Proc. Natl. Acad. Sci.*, 1986, vol. 87, pp. 2934–2938.
Plum, GE et al., "Thermodynamic Characterization of the Stability and the Melting Behaviour of a DNA Triplex: A Spectroscopic and Calorimetric Study", *Proc. Natl. Acad. Sci.*, 1990, vol. 87, pp. 9436–9440.
Postel, EH et al., "Evidence That a Triplex–Forming Oligodeoxyribonucleotide Binds to the C–myc Promoter in HeLa Cells, Thereby Reducing C–myc mRNA Levels", 1991, vol. 88, 3 pages.
Povsic, TJ et al., "Triple Helix Formation by Oligonucleotides on DNA Extended to the Physiological pH Range", *J. Am. Chem. Soc.*, 1989, vol. 111, pp. 3059–3061.

(List continued on next page.)

*Primary Examiner*—Donna Wortman
(74) *Attorney, Agent, or Firm*—Rothwell, Figg, Ernst & Manbeck, p.c.

(57) ABSTRACT

Disclosed are methods for detecting in situ the presence of a target sequence in a substantially double-stranded nucleic acid segment, which comprises: a) contacting in situ under conditions suitable for hybridization a substantially double-stranded nucleic acid segment with a detectable third strand, said third strand being capable of hybridizing to at least a portion of the target sequence to form a triple-stranded structure, if said target sequence is present; and b) detecting whether hybridization between the third strand and the target sequence has occured.

26 Claims, 7 Drawing Sheets

OTHER PUBLICATIONS

Roberts, RW et al., "Specificity and Stringency in DNA Triplex Formation", *Proc. Natl. Acad. Sci.*, 1991, vol. 88, pp. 9397–9401.

Rougée, M et al., "Kinetics and Thermodynamics of Triple-Helix Formation: Effects of Ionic Strength and Mismatches," *Biochemistry*, 1992, vol. 31, pp. 9269–9278.

Singleton, SF et al. "Influence of pH on the Equillibrium Association Constants for Oligodeoxyribonucleotide–Directed Triple Helix Formation at Single DNA Site", *Biochemistry*, 1992a, vol. 31, pp. 10995–11003.

Singleton, SF et al., "Thermodynamics of Oligodeoxyribonucleotide–Directed Triple Helix Formation: An Analysis Using Quantitative Affinity Cleavage Titration", *J. Am. Chem. Soc.*, 1992b, vol. 114, pp. 6957–6965.

Strobel, SA et al., "Site–Specific Cleavage of Human Chromosome 4 Mediated By Triple–Helix Formation", *Science*, 1991, vol 254, 1639–1642.

Trask, BJ, "DNA Sequence Localization in Metaphase and Interphase Cells by Fluorescence in Situ Hybridization", *Methods Cell Biol.*, 1991, vol. 35, pp. 3–35.

Warburton, PE et al., "Genomic Analysis of Sequence Variation in Tandemly Repeated DNA. Evidence for Localized Homogeneous Sequence Domains within Arrays of α–Satellite DNA", *J. Mol. Biol.*, 1990, vol. 216, pp. 3–16.

Warbruton, PE et al., "PCR Amplification of Tandemly Repeated DNA: Analysis of Intra– and Interchromosomal Sequence Variations and Homologous Unequal Cross–over in Human alpha Satellite DNA", *Nucleic Acids Res.*, 1992, vol. 20, pp. 6033–6042.

Warburton, PE et al., "Interhomologue Sequence Variation of Alpha Satellite DNA from Human Chromosome 17: Evidence for Concerted Evolution Along Haplyotypic Lineages", *J. Mol. Biol.*, 1995, vol. 41, pp. 1066–1015.

Waye, JS et al., "Structure, Organization, and Sequence of Alpha Satellite DNA from Huma Chromosome 17: Evidence for Evolution by Unequal Crossing–Over and an Ancestral Pentamer Repeat Shared with the Human X Chromosome", *Mol. Cell Bil.*, vol. 6, pp. 3156–3165.

Waye, JS et al., "Molecular Analysis of a Deletion Polymorphism in Alpha Satellite of Human Chromosome 17: Evidence for Homologous Unequal Crossing–Over and Subsequent Fixation", *Nucleic Acids Res.*, 1986, vol. 14, pp. 6915–6927.

Wevrick, R et al., "Long–Range Organization of Tandem Arrays of Alpha Satellite DNA at the Centromeres of Human Chromosomes: High–Frequency Array–Length Polymorphism and Meotic Stability", *Proc. Natl. Acad. Sci.*, 1989, vol. 86, pp. 9394–9398.

Willard, HF et al., "Hierarchical Order in Chromosome–Specific Human Alpha–Satellite Human Alpha–Satellite DNA", *Trends Genet.*, 1987, vol. 3, pp. 192–198.

Willard, HF et al., "Detection of Restriction Fragment Length Polymorphisms at the Centromeres of Human Chromosomes by Using Chromosome–Specific α Satellite DNA probes: Implications for Development of Centromere–Based Genetic Linkage Maps", *Proc. Natl. Acad. Sci. USA*, 1986, pp. 5611–5615.

Willard, HF et al., "Molecular Organization and Haplotype Analysis of Centrometric DNA from Human Chromosome 17: Implications for Linkage in Neurofibromatosis", *Genomics*, 1987, vol. 1, p. 368–373.

Xodo, LE et al., "Effect of 5–Methylcytosine on the Stability of Triple–Stranded DNA—A Thermodynamic Study," *Nucleic Acids Research*, 1991, vol. 19, No. 20, pp. 5625–5631.

Yoon, K et al., "Elucidation of the Sequence–Specific Third-Strand Recognition of Four Watson–Crick Base Pairs in a Pyrimidine Triple–Helix Motif: T–AT, C–CG, T–GC, and G–TA", *Proc. Natl. Acad. Sci. USA*, 1992, vol. 89, pp. 3840–3844.

* cited by examiner

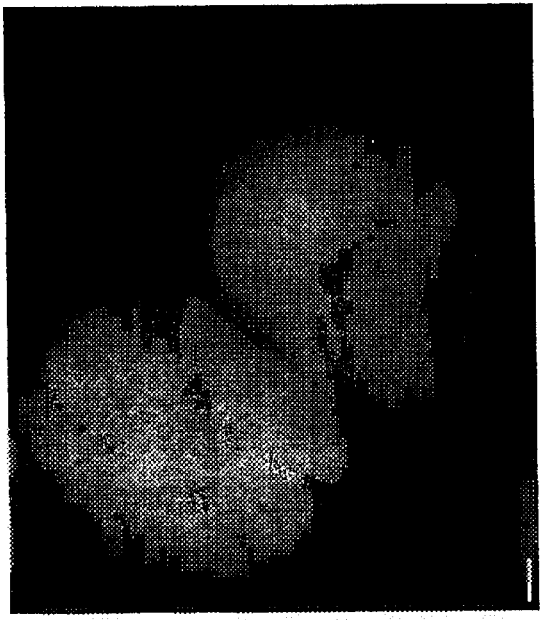
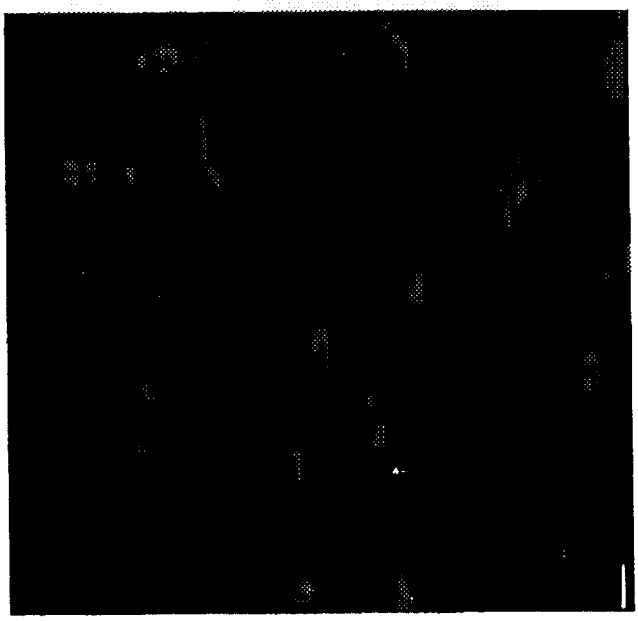
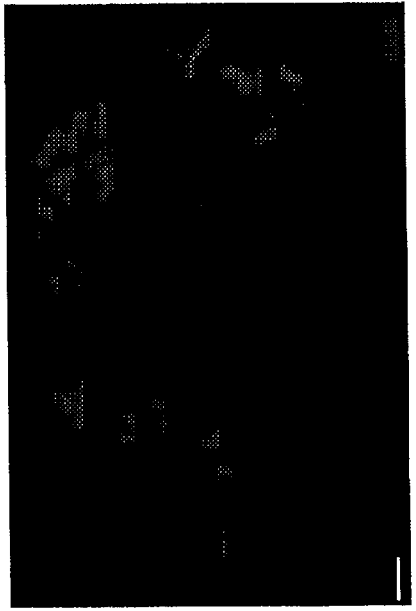
FIG. 5A
FIG. 5B
FIG. 5C

TRIPLEX IN-SITU HYBRIDIZATION

CROSS-REFERENCES TO RELATED APPLICATIONS

This application is a 371 of PCT/US98/23765 filed Nov. 10, 1998, which claims benefit of U.S. Ser. No. 60/064,997 filed Nov. 10, 1997.

STATEMENT REGARDING FEDERALLY SPONSORED RESEARCH OR DEVELOPMENT

The present work was supported by grants from the National Institutes of Health (GM42936) and the Department of Energy (DE-FG02-96ER62202).

BACKGROUND OF THE INVENTION

1. Field of the Invention

The present invention relates to methods for identifying and classifying nucleic acids by means of in situ hybridization of a third-strand probe to a duplex DNA target.

2. Description of Related Art

A list of the references referred to by number herein is found at the end of the Detailed Description of the Invention herein.

Oligodeoxy- and ribo-nucleotide 'third strands' bind in sequence- and polarity-specific alignment within the major groove of cognate purine-rich•pyrimidine-rich nucleic acid duplex target sequences (1). A third-strand binding code has been elucidated (2) that encompasses triplexes of various structural motifs, of which the best characterized is the pyrlmidine-parallel (Y:R•Y) with T:A•T and $C^+$:G•C triplets. The fidelity of third-strand binding to cognate targets of equal and lesser length, targets contained within large DNA molecules, and targets with inverted base pairs, i.e., R•Y→Y•R, is well documented (3). Optimal solution conditions for third-strand binding, i.e., pH, counterionic strength, and temperature, can be manipulated to induce third-strand dissociation or prevent association. While certain triplet mismatches are moderately tolerated within the Y:R•Y motif (4), e.g., T:C•G and G:T•A, others are especially destabilizing. Such destabilization provides temperature as a variable to selectively favor, under in vitro and demonstrated in situ conditions, desired triplexes over less perfect ones, as required in the large non-specific duplex DNA background of the human genome, while maintaining essentially constant pH and ionic strength.

The use of third strands for sequence-specific recognition of human genomic DNA has been exploited for the development of potential anti-gene therapeutic agents (5) and artificial endonucleases (6). By virtue of the present invention, this approach is extended to in situ hybridization for the detection and analysis of nucleic acids.

SUMMARY OF THE INVENTION

The present invention provides a method for detecting in situ the presence of a target sequence in a substantially double-stranded nucleic acid segment, which comprises:

a) contacting in situ under conditions suitable for hybridization a substantially double-stranded nucleic acid segment with a detectable third strand, said third strand being capable of hybridizing to at least a portion of the target sequence to form a triple-stranded structure, if said target sequence is present in the nucleic acid segment; and b) detecting whether hybridization between the third strand and the target sequence has occurred.

BRIEF DESCRIPTION OF THE DRAWINGS

FIGS. 5A–5C are TISH images of (A) a non-denatured mouse×human chr. 17 metaphase spread and (B) nuclei hybridized with the chr. 17 -satellite-specific third strand 5'-Pso-$Tm^5C$-Bio-3'. FITC-avidin-based detection is specific for the single human chr.17s. FIG. 5C is a TISH image showing a competition assay that demonstrates specificity of third-strand binding to chr.17 -satellite in human metaphase spreads. A 25:1 molar ratio of 5'-Tm$^5$C-3' to 5'-Pso-Tm$^5$C-Bio 3' effectively competes out the dual modified third-strand. The white bar at the bottom left of each micrograph represents 10 microns.

FIGS. 6(B) and 6(D) are their corresponding +17/+17 FISH images.

DETAILED DESCRIPTION OF THE INVENTION

Third Strand

Figure 1A:
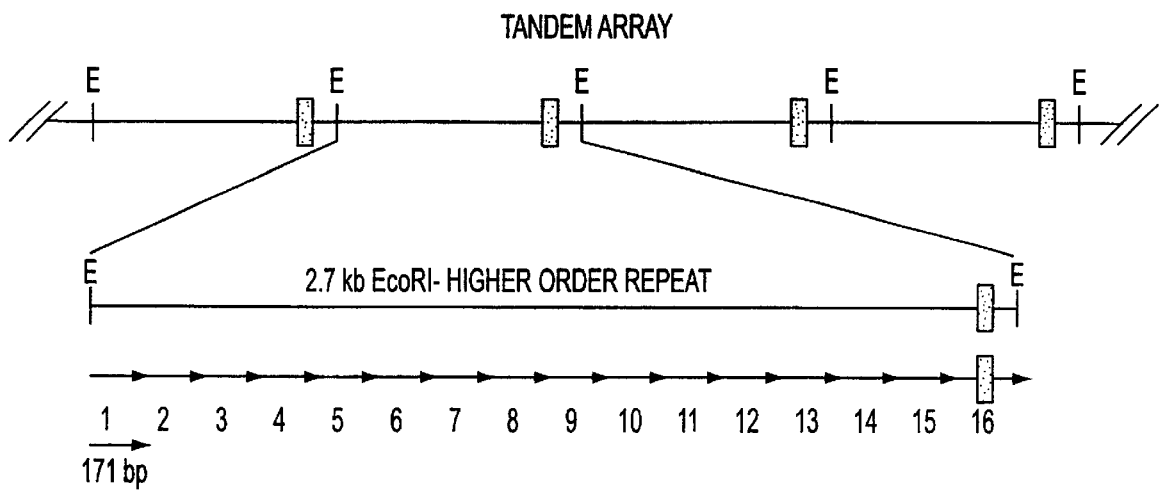
FIG. 1A depicts the organization of chromosome 17 -satellite DNA. A tandem array of the chr.17 2.7 kb EcoRI (E) higher-order repeat, single higher-order repeat, and the sixteen 171 bp monomer units that comprise it. Gray rectangles represent the unique 16 bp third-strand target sequence within each monomer sixteen.

The third strand is a synthetic or naturally occurring oligonucleotide capable of binding with specificity to a predetermined target region of a double-stranded nucleic acid molecule to form a triple-stranded structure. The third strand may bind solely to one strand of the native nucleic acid molecule, or may bind to both strands at different points along its length.

Preferably, the oligonucleotide probe is a single-stranded DNA molecule between about 7 and about 50, most preferably between about 10 and about 23 nucleotides in length. Its base composition can be homopurine, homopyrimidine, or a mixture of purines and pyrimidines. The third-strand binding code and preferred conditions under which a triple-stranded helix will form are well known to those skilled in the art (U.S. Pat. No. 5,422,251; Beal and Dervan, *Science* 251: 1360 (1991); Beal and Dervan, *Nucleic Acids Res.*, 20:2773 (1992); Broitman and Fresco, *Proc. Natl. Acad. Sci. USA*, 84:5120 (1987); Fossella, et al., *Nuc. Acids Res.* 21:4511 (1993); Letai, et al., *Biochemistry* 27:9108 (1988); Sun, et al., *Proc. Natl. Acad. Sci. USA* 86:9198 (1989)). Briefly, adenosine, uridine, thymidine and inosine in the third strand will bind to adenosine in the duplex, and guanosine, cytidine and inosine in the third strand will bind to guanosine in the duplex. The third strand need not be perfectly complementary (in the binding code sense, not in the Watson-Crick sense) to the duplex, but may be substantially complementary. In general, by substantially complementary is meant that one mismatch is tolerable in about every 10 base pairs.

The third strand may have a natural phosphodiester backbone or may be comprised of other backbone chemical groups or mixtures of chemical groups which do not prevent the triple-stranded helix from forming. These alternative chemical groups include phosphorothioates, methylphosphonates, peptide nucleic acids (PNAs), and others known to those skilled in the art. Preferably, the third-strand backbone is phosphodiester.

The third strand may also comprise one or more modified sugars, which would be known to those skilled in the art. An example of such a sugar includes α-enantiomers.

The third strand may also incorporate one or more synthetic bases if such is necessary or desirable to improve third-strand binding. Examples of synthetic base design and the bases so designed are found in the co-pending U.S. application Ser. No. 08/473,888 of Fresco, et al. entitled "Residues for Binding Third Strands to Complementary Nucleic Acid Duplexes of any Base-Pair Sequence", filed Jun. 7, 1995, and published as WO/9641009, the contents of which are incorporated herein by reference.

If it is necessary to protect the third strand from nucleases resident in the target cells, the third strand may be modified with one or more protective groups. In a preferred embodiment, the 3' and 5' ends may be capped with a number of chemical groups known to one of ordinary skill, such as alkyl amines, acridine, cholesterol, etc. In another embodiment, the third strand may be protected from exonucleases by circularization.

Label

The third strand should include a reporter group which has a physical or chemical characteristic which can be measured or detected by appropriate detector systems or procedures, which will allow detection of triplex formation. Detectability can be provided by such characteristics as color change, luminescence, fluorescence or radioactivity, or it can be provided by the ability of the reporter group to serve as a ligand recognition site. Such characteristics can be measured or detected, for example, by the use of conventional calorimetric, spectrophotometric, fluorometric or radioactivity sensing instrumentation, or by visual inspection, e.g., microscopic observation.

The interactions which can be usefully initiated by the reporter group include appropriately specific and selective interactions productive of groups or complexes which are themselves detectable, for example, by colorimetric, spectrophotometric, fluorometric or radioactive detection procedures. Such interactions can take the form of protein-ligand, enzyme-substrate, antibody-antigen, carbohydrate-lectin, protein-cofactor, protein-effector, nucleic acid-nucleic acid, and nucleic acid-ligand interactions. Examples of such ligand-ligand interactions include fluorescein-antifluorescein antibody, dinitrophenyl-dinitrophenyl antibody and biotin-avidin. Either one of each of such ligand pairs may serve as a ligand recognition type reporter group. Preferred reporter groups of the present invention include, for example, biotin, fluorescein, digoxigenin, phenyloxazolone, tetramethyl rhodamine, Texas Red, and BODIPY (contains the 4,4-difluoro-4-bora-3a,4a-diaza-s-indacene unit).

General methods for joining the reporter group to the third strand are well known to those skilled in the art. Examples of those methods may be found, for example, in U.S. Pat. Nos. 4,711,955 and 5,684,142.

Target

The substantially double-stranded nucleic acid segment may comprise any combination of naturally occurring nucleic acid types, such as two DNA strands, two RNA strands, or a DNA-RNA hybrid. By "substantially double-stranded" is meant that the two strands which make up the nucleic acid segment need not be hybridized to each other along their entire length. It is preferred that the target sequence to which the third strand binds is completely double-stranded, but a degree of non-binding between the two strands of the target sequence is tolerable, so long as it does not exceed about 1 mismatch in 10 base pairs.

The target sequence may be any sequence for which detection is desired, and may be anywhere along the length of DNA or RNA found in a cell, including α-satellite regions, other satellite regions, non-satellite heterochromatin, or euchromatin regions. The target sequence may be within the chromosomal region of a eukaryotic species, particularly organisms of commercial significance in agriculture, or the double-stranded stage of a virus.

The in situ hybridization may take place in environments known to those skilled in the art, and are in most respects similar to those used for conventional in situ hybridization on denatured nucleic acids, although according to the present invention the target sequence is not denatured. The present hybridization may be performed on metaphase spreads and interphase nuclei, the preparation of which would be readily apparent to those skilled in the art. The major difference from conventional in situ hybridization is that in performance of the present invention, the hybridization conditions (e.g., temperature, pH,. salt concentration, etc.) are non-denaturing and should be such that, as described above, the target nucleic acid segment is substantially double-stranded.

It is preferred that the target sequence contain a purine-rich segment on one strand and a complementary pyrimidine-rich segment on the other strand. A stretch of at least ten consecutive purine bases is particularly preferred.

Binding Enhancement

The oligonucleotide may be modified to include a moiety which will enhance the binding of the third strand to the target sequence. Such a moiety may be positioned anywhere along the length of the third strand. Suitable moieties include well known DNA-binding, cross-linking or intercalating agents such as psoralen, acridine, coralyne, etc. The binding moiety is often incorporated into the oligonucleotide during its synthesis. For example, commercially available compounds such as psoralen C2 phosphoroamidite (Glen Research, Sterling Va.) are inserted into a specific location within an oligonucleotide sequence in accordance with the methods of Takasugi, et al., *Proc. Natl. Acad. Sci USA*, 88:5602 (1991); Gia, et al., *Biochemistry* 31:11818 (1992); Giovannangeli, et al., *Proc. Natl. Acad. Sci. USA*, 89:8631 (1992), all of which are incorporated by reference herein. The binding moiety may also be attached to the oligonucleotide through a linker, such as sulfo-m-maleimidonbenzoly-N-hydroxysuccinimide ester (sulfo-MBS, Pierce Chemical Company, Rockford Ill.) in accordance with the methods of Liu, et al., *Biochem.* 18:690 (1979) and Kitagawa and Ailawa, *J. Biochem.* 79:233 (1976), both of which are incorporated by reference herein.

Utility

Third-strand in situ hybridization (TISH) complements and extends denaturant Watson-Crick-based FISH (7) technology to permit molecular cytogenetic and biochemical studies of non-denatured metaphase and interphase fixed chromosomes and chromatin, though it is not restricted to such uses. In Table 1 below, we have identified unique multicopy α-satellite third-strand target sequences in 22 of 24 human chromosomes, making centromere-specific chromosome identification by TISH applicable to virtually all human chromosomes. In the Table, third-strand target sequences (Column 2) within the -Satellite DNA of a particular human chromosome type or chromosome group, e.g., 1, 15, 16 (Column 1) are given. Numbers after the decimal indicate that different third-strand target sequences are shared within a group or are unique to a single chromosome. Group (1, 15, 16) has three target sequences. Chromosome 3 contains four uniquely different target sequences.

TABLE 1

| Chromosome Type or Group | Target Sequence | |
|---|---|---|
| 1.1 | AGTAAAGGAA AGAA | [SEQ ID NO:3] |
| 1, 15, 16.1 | TATTTCCTTT TCTCGCTT | [SEQ ID NO:4] |
| 1, 15, 16.2 | GAATGAAAAG GAAAG | [SEQ ID NO:5] |
| 1, 15, 16.3 | TTTCCTTTTC TCGCTTT | [SEQ ID NO:6] |
| 1, 5, 19.1 | AAAGGTAGAA AAGGAAATA | [SEQ ID NO:7] |
| 1, 5, 19.2 | AAAGGCAGAA AAGGAAATA | [SEQ ID NO:8] |

TABLE 1-continued

| Chromosome Type or Group | Target Sequence | |
|---|---|---|
| 1, 5, 19.3 | CTTTTCTTTT TCATTC | [SEQ ID NO:9] |
| 2.1 | CCTTTCTTTT GAGAGAGCAG | [SEQ ID NO:10] |
| 2, 20.1 | GAAAAAGGAA ATATCTTCCC CT | [SEQ ID NO:11] |
| 3.1 | TTTACCCCTT TCTTTTC | [SEQ ID NO:12] |
| 3.2 | GATAGAAAAG GAAA | [SEQ ID NO:13] |
| 3.3 | GGTAGAAAAG GAAA | [SEQ ID NO:14] |
| 3.4 | CTTTCCTTTA GAAAACAGCA GAG | [SEQ ID NO:15] |
| 5.1 | GGAAAAkAG GATA | [SEQ ID NO:16] |
| 5.2 | CTTTCTCCTT ACTT | [SEQ ID NO:17] |
| 6.1 | GAAAAGGGAG GTTTCACTCT TT | [SEQ ID NO:18] |
| 6.2 | CTTTCTCTAC CAAAAGAAAG G | [SEQ ID NO:19] |
| 7.1 | GGTGAAAATG GAAAAGGAAA | [SEQ ID NO:20] |
| 7.2 | GAGGCAAATG GAGAAAAAG | [SEQ ID NO:21] |
| 7.3 | TCCTTTCTTT TCATTC | [SEQ ID NO:22] |
| 7.4 | ACAGAGGAAA AGGAAA | [SEQ ID NO:23] |
| 7.5 | ATGGAGGAAA AGGAAA | [SEQ ID NO:24] |
| 9.1 | AGAGATGAAC CTTTCTTTTT | [SEQ ID NO:25] |
| 10.1 | ACGGGGAGAA AGGAAATA | [SEQ ID NO:26] |
| 10.2 | ATGGAGAGAA AGGAAATA | [SEQ ID NO:27] |
| 10.3 | AGAGGGAGCA GAGGTGAAA | [SEQ ID NO:28] |
| 10.4 | TTTCTCCTTT CTCTTCAT | [SEQ ID NO:29] |
| 10.5 | TTCCACCTTT CTTTTC | [SEQ ID NO:30] |
| 10.6 | CCTTTCTTGA GAGAGAGCAG A | [SEQ ID NO:31] |
| 10.7 | TTTCACCTTT CTCTTC | [SEQ ID NO:32] |
| 10.8 | CCTTCCTTTA GAGAGAGCAG A | [SEQ ID NO:33] |
| 10, 12.1 | AAAGGTAGAA AAGGAAACA | [SEQ ID NO:34] |
| 10, 12.2 | GAAGAGAAAG GTGAAA | [SEQ ID NO:35] |
| 10, 12.3 | CCTTTCTTTT GATGGAGGAG | [SEQ ID NO:36] |
| 10, 12.4 | CTCTCTCTAA AGAAAGG | [SEQ ID NO:37] |
| 10, 12.5 | AAAGGTAGAA AAGGAAATA | [SEQ ID NO:38] |
| 12.1 | CCTTTCTTTT GATGAAGGAG | [SEQ ID NO:39] |
| 12.2 | GGAAACGGGA TTTCTTCCT | [SEQ ID NO:40] |
| 12.3 | CCTTTCTTTT GATGAAGGAG | [SEQ ID NO:41] |
| 13, 21.1 | GGTGAAAAAG GGAA | [SEQ ID NO:42] |
| 13, 21.2 | GAAAAAGGGA ATGTCTTCCC | [SEQ ID NO:43] |
| 13, 21.3 | AGAGTGGAAC CTCTCTCTTT T | [SEQ ID NO:44] |
| 14, 22.1 | GGTGAGAAAG GAAA | [SEQ ID NO:45] |
| 14, 22.2 | AGAGGTGGAT CTTTCTTTT | [SEQ ID NO:46] |
| 14, 22.3 | AAAGGAATA TCTTCCCCT | [SEQ ID NO:47] |
| 14, 22.4 | GGTGAAAAGG GAAA | [SEQ ID NO:48] |
| 14, 22.5 | GAAAAGGGAA ATATCTTCTC | [SEQ ID NO:49] |
| 14, 22.6 | AACAGAGAAG AACCTTCCTT TT | [SEQ ID NO:50] |
| 16.1 | TTTCACCTTT CTTTTC | [SEQ ID NO:51] |
| 17.1 | AGAAAGAAGA CAGAAG | [SEQ ID NO:52] |
| 17.2 | AAAAAGAAGA CAGAAG | [SEQ ID NO:53] |
| 17.3 | TTTTTTTTCC TCTCT | [SEQ ID NO:54] |
| 17.4 | CTTTCCTTTC GAGAGAAG | [SEQ ID NO:55] |
| 17.5 | ITTTCCTTTC GAGAGAGAAG | [SEQ ID NO:56] |
| 17.6 | GGAAAAGGAA TTATCTTTCC C | [SEQ ID NO:57] |
| 18.1 | AAGGTGAAAA AGGAAA | [SEQ ID NO:58] |
| 18.2 | ATGGAGAGAA AGGAAA | [SEQ ID NO:59] |
| 18.3 | AAGGTGAAAA AGAAA | [SEQ ID NO:60] |
| 18.4 | AAAGGAGTAG AACCTTTCTT TTC | [SEQ ID NO:61] |
| 20.1 | GGTGAAAAG GAGA | [SEQ ID NO:62] |
| 20.2 | GGTGAAAAAG GAAA | [SEQ ID NO:63] |
| 20.3 | GAAAAAGGAA ATATCTTCCC | [SEQ ID NO:64] |
| 22.1 | GGTGGAGAAG GAAA | [SEQ ID NO:65] |
| 22.2 | GGAAAAGAAT TATCTTCTC | [SEQ ID NO:66] |
| 22.3 | GGTGGAAAAG GAAA | [SEQ ID NO:67] |
| 22.4 | AGTGGAAAAG GAAA | [SEQ ID NO:68] |
| 22.5 | TTCCCTTTCA GAGAGCAG | [SEQ ID NO:69] |
| 22.6 | AAAGGAAATA TCTTCCCCT | [SEQ ID NO:70] |
| X.1 | ACAGAAAGAC GAGAGAGAAG CA | [SEQ ID NO:71] |
| X.2 | CCTTTTCCTT TATCTTC | [SEQ ID NO:72] |

TABLE 1-continued

| Chromosome Type or Group | Target Sequence |
|---|---|
| X.3 | GGAAAAGGAA ATATCTTCTC [SEQ ID NO:73] C |
| Y.1 | GGAAGATGGT GGAAAAGGAA [SEQ ID NO:74] A |
| Y.2 | GGAAAAGGAA GTATCTTCCT [SEQ ID NO:75] |

TISH is also applicable to other multicopy sequences, as well as to single copy sequence identification, if those sequences are amenable to third-strand binding. In that event, they would have the same utility as FISH for diagnosing genetic disorders, screening for individuals at risk for developing genetic-based diseases, and for diagnosing infectious diseases by detecting the presence of target sequences unique to a pathogen. Complementary diagnostic roles for chromosome-specific α-satellite third-strand probes are as determinants of numerical chromosome abnormalities, i.e., aneuploidy (e.g., trisomy 21), in metaphase and interphase cells of tumors, and of individuals with genetic disorders. TISH-based aneuploid detection is particularly advantageous for those cell types having small nuclear volumes and extremely condensed chromatin, e.g., uncultured prenatal amniocyte fluid cells and spermatozoa, since interphase chromatin denaturation is not required, and third-strand penetration of such nuclei under solution conditions may be more efficient. It is also noted that while FISH and G-banding are incompatible, the former requiring denatured chromosomal DNA and the latter non-denatured DNA, TISH shares that requirement with G-banding, so that those two techniques are applicable to the same mitotic chromosome preparations. In addition, the meiotic stability of chromosome-specific α-satellite polymorphisms (8, 9) should, in cases where third-strand target sequences are heteromorphic, e.g., D17Z1, permit TISH to serve as a rapid assay for Mendelian segregation analysis.

Third-strand hybridization of chromosome-specific α-satellite probes to interphase chromatin within nuclei may provide a tool for studying chromosome organization under aqueous conditions. Hybridization of such probes to native metaphase chromosomes within mitotic cells in suspension also makes possible third strand-based chromosome-specific univariate flow sorting.

The use and novel features of the present invention will be further understood in view of the following non-limiting examples.

EXAMPLE 1

Selection of Chromosome 17 α-Satellite Target Sequence

GenBank, EMBL, and GB_New databases were searched for human o-satellite sequences using GCG software (10), and a Homo sapiens α-satellite database was constructed from 336 sequence entries containing confirmed nucleotide sequences. This database was then searched to identify same strand and alternate strand (i.e., where the target sequence switches from one duplex strand to the other) homopurine•homopyrimidine runs of defined length and specificity. Mismatches due to inverted base pairs (base pairs with a pyrimidine residue in the predominantly purine-containing target strand) were limited to one per ten residues (2/20, 3/30, etc.); and the position (internal vs. terminal) and relation (adjacent vs. separate) of two or more mismatches was considered when purine-rich•pyrimidine-rich runs exceeded 19 residues.

Three same strand and three alternate strand target sequences of varying specificities were identified for chromosome 17. The nucleotide sequence of the chromosome 17 2.7 kb α-satellite higher-order repeat in recombinant clone p17H8 (11) was searched for matches to the six potential target sequences. Identical sequences were found in higher-order repeat monomers 11 and 16 for one alternate and one same strand target sequence, respectively. Similar sequences with mismatches were found for two others, one differing from the monomer 16 sequence by a single point mutation, and no matches were found for the remaining two. The unique 16 bp purine-rich•pyrimidine-rich chromosome 17 α-satellite sequence located in monomer 16, and contained on p17H8, was selected for in vitro and in situ third-strand targeting.

Molecular Organization of Chromosome 17 α-Satellite and Target

The predominant organization of α-satellite at the D17Z1 locus of chromosome 17 (FIG. 1A) from recombinant clone p17H8 (11), is representative of the general tandem molecular organization of the complement of α-satellites (12). The D17Z1 locus consists of an array of tandem 2.7 kb higher-order repeat units, themselves composed of 16 divergent monomer sequences, each ~171 bps in length. The 500–1000 tandem repeats separated by unique EcoR1 restriction sites at their junctions, gives rise to arrays of 1–2 million base pairs. Less abundant 15- and 14-monomer repeat units, EcoR1 heteromorphs, are also found constituitively on chromosome 17, with the 15- and 14-mers shown to be essentially identical in sequence to the 16-mer, excluding just 1 and 2 tandem monomers, respectively (11, 13).

The chromosome 17 alpha-satellite sequence selected as the target for third-strand binding should be unique, multicopy, and chromosome-specific. The complete nucleotide sequence of the 2.7 kb higher-order repeat on chromosome 17 (11) shows substantial sequence divergence (up to ~30%) among its sixteen 171 bp monomers, but not within the 16 bp third-strand target sequence. Independent clones of this tandem 2.7 kb higher-order repeat are >99% identical. Moreover, sequence comparisons among the multimeric alpha-satellite higher-order repeats of human chromosomes show at least 15–30% divergence (12).

The purine-rich DNA target strand,
AAAAAGAAGA CAGAAG [SEQ ID NO:1] of the selected 16 bp chromosome 17 α-satellite target sequence is interrupted by one pyrimidine (C) residue. Within the megabase chromosome 17 α-satellite array, this 500–1000 times-repeated target sequence occurs once within monomer 16 of each tandem 2.7 kb higher-order repeat (11) (FIG. 1A). Within simple sequence DNA, the chance occurrence of any 16 bp sequence is 416 or 1 in $4.3 \times 10^9$. Hence, the probability of a non-alpha satellite location for the multicopy chromosome 17 target sequence should be remote in the $3 \times 10^9$ base pair haploid human genome.

Oligodeoxyribonucleotide Third Strand Probe

Figure 1B:
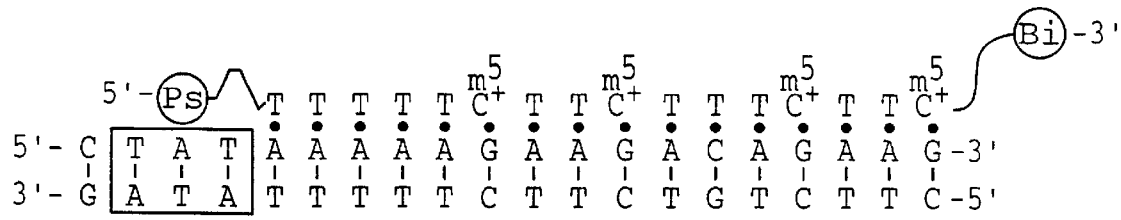
FIG. 1B depicts the 16-nt third strand [SEQ ID NO.2] and its 16 bp -satellite target [SEQ ID NO.76] and [SEQ ID NO.77]. Third strand T and $m^5C^+$ residues are bound via Hoogsteen-hydrogen bonds (•) to the purine residues of their Watson-Crick (|) target [SEQ ID NO.76]. The boxed sequence shows the upstream -satellite DNA T residues capable of forming photoadducts with the psoralen (4'-hydroxymethyl-4,5',8-trimethylpsoralen, HMT) moiety of the dual-modified third strand. Ps=psoralen; Bi=biotin.

The 16 nucleotide homopyrimidine third strand DNA probe:
TTTTTCTTCT TTCTTC [SEQ ID NO:2] modified at its 5' and 3' termini with psoralen and biotin, respectively, binds the 16 bp α-satellite target sequence in parallel orientation to its purine strand complement (FIG. 1B). $m^5C$ (5-methylcytosine) residues were substituted for C to afford greater affinity for target G•C base pairs (14). Binding specificity of this third strand to its purine-rich target is derived from the formation of 15 canonical triplets, 11 T:A•T and 4 m⁵C⁺:G•C. The non-canonical T:C•G triplet sandwiched between T:A•T nearest neighbors is only moderately destabilizing on similar Y:R•Y triplexes (4).

The [SEQ ID NO:2] third strand and its dual 5'-psoralen- and 3'-biotin-modified version were synthesized by the β-cyanoethyl phosphoramidite method with an Applied Biosystems Synthesizer 380B. A psoralen (4'-hydroxymethyl-4,5',8-trimethylpsoralen, HMT) C6 phosphoramidite and biotin TEG-CPG column (both Glen Research) were used to incorporate psoralen and biotin at respective 5' and 3' termini. The annotation 5'-Pso-Tm⁵C-Bio-3' represents dual psoralen- and biotin-modified third strands, and 5'-Tm⁵C-3', the non-modified form.

Crude synthesis products were analyzed by PAGE and UV shadowing. Oligomers were gel purified, desalted using Water's Sep Pak C18 cartridges, lyophilized, and stored at −20° C. in sterile water. The concentration of oligonucleotides was determined in ddH$_2$O at A$_{260}$ using extinction coefficients of 8800 and 5700 M$^{-1}$ cm$^{-1}$ for dT and dm⁵C residues, respectively.

Cocktail for Third-Strand In Vitro and In Situ Hybridization

Both quantitative solution and in situ third-strand hybridization assays were carried out in 25 μl of 10 mM Bis-Tris HCl-buffered cocktail at pH 6.0 containing optimal concentrations of mono-, di-, and polyvalent cations (50 mM K⁺/10 MM Mg$^{2+}$/1 μM spermine$^{4+}$), reducing and chelating agents (1 mM DTT and 1 mM EDTA), a molecular crowding agent (2% PEG 8000), deionized formamide (1.0–2.5%), and alcohol-precipitated (100–300 nt) total yeast RNA (1.0 ng). For in situ hybridization, the chaotropic agent formamide was used at low concentrations (≦2.5%) to reduce the capillary adhesion between glass microscope slide and coverslip surfaces, so as to promote third-strand equilibration across the total hybridizable surface area. Formamide at these concentrations lowers the Tm of duplex DNA by only 0.7–1.75° C. Yeast RNA was used to compete out non-specific binding of third strands to glass surfaces and cellular debris. Neither deionized formamide nor yeast RNA at these concentrations affect the specificity or affinity of third-strand binding to the p17H8 chromosome 17 target sequence in solution.

Third-Strand In Vitro Hybridization and Binding Specificity

Optimized solution binding assays confirmed third-strand binding specificity to chromosome 17 α-satellite target sites in various sized recombinant DNAs (5.7 to 50 kb) (15). One such assay is shown to demonstrate third-strand binding specificity to this target in a supercoiled plasmid; another, to confirm that this specificity is not diminished in the presence of a human chromatin background similar in DNA sequence complexity to a fixed protein-depleted mitotic spread.

Figure 2A:
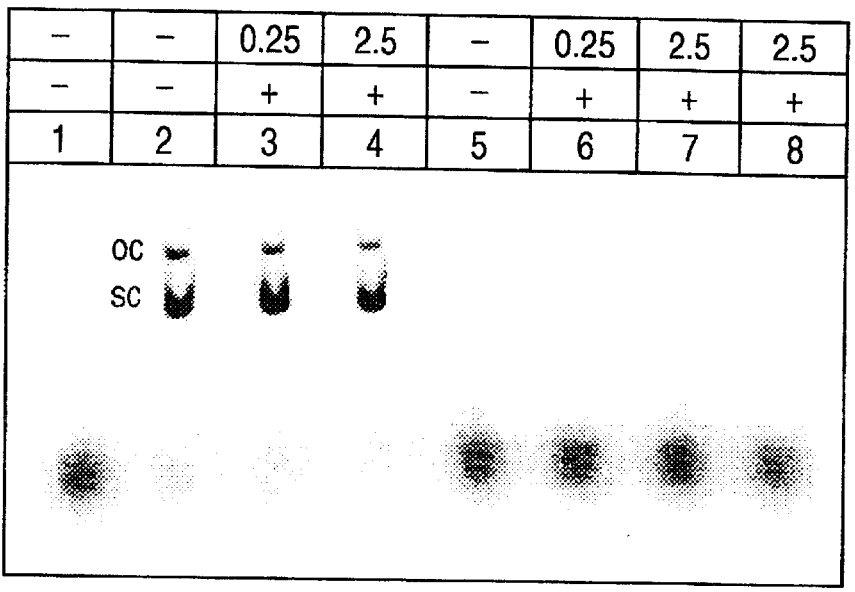
FIG. 2A is an autoradiograph showing the specificity of third-strand binding to supercoiled (sc) p17H8. Gel purified $^{32}$P-end-labeled 5'-$Tm^5C$-3' ($8\times10^6$ cpm/pmol) and 0.25 µg of 2×CsCl p17H8 or pMJ1 were mixed at 1:1 oligomer:plasmid molar ratio in 1×triplex cocktail±deionized formamide (0.25 or 2.5%) and yeast RNA (1 ng) at pH 6.0 and 23° C. for ~20 hrs to attain equilibrium. 25 µl rxn samples were electrophoresed on a 0.8% SeaKem Gold (FMC) agarose gel overnight at 23° C. and 1.3 V/cm with buffer recirculation. Pre-flashed film (Dupont Reflection) was exposed to the dried gel at 4° C. for 15 min. Control lanes 1 and 8 contain $^{32}$P-third strand alone, lanes 2–4 $^{32}$P-third strand and p17H8, and lanes 5–7 $^{32}$P-third strand and pMJ1 (lacking target).

Thus, incubation of radiolabeled third-strand probe lacking psoralen and biotin moieties, 5'-Tm⁵C-3', with different supercoiled plasmid substrates demonstrated that third-strand binding is specific for the plasmid carrying the 16 bp α-satellite target sequence. Plasmid substrates were p17H8 (5.7 kb), which contains the complete 2.7 kb chromosome 17 α-satellite higher-order repeat, and pMJ1 (~5.5 kb), a p17H8 deletion-derivative lacking the target sequence and an additional 158 bp of monomer 16 but containing monomers 1–15. Supercoiled p17H8 and pMJ1 were mixed with $^{32}$P-end-labeled third strand at an oligomer:plasmid molar ratio of 1:1 in 1×triplex cocktail±formamide (0.25 or 2.5%) and yeast RNA (1.0 ng) at pH 6.0 and 23° C. for ~20 hrs to attain equilibrium. FIG. 2A shows $^{32}$P-label at gel positions corresponding to supercoiled (sc) and open circular (oc) p17H8 (lanes 2–4). The deletion plasmid pMJ1, which lacks the target sequence but contains monomers 1–15, was not bound by the labeled third strand (lanes 5–7).

The degree of sequence similarity between each of the 16–171 bp monomers that make up the α-satellite higher-order repeat of chromosome 17 provides an "internal control" for third-strand binding specificity. Sequences in monomers 1–15 are similar in length and base composition to the monomer 16 target sequence, one differing from it by only two bases (11). Hence, this solution binding assay shows that, under the conditions employed, third-strand binding is highly specific for the 16 bp sequence within monomer 16 of the 2.7 kb chromosome 17 α-satellite repeat on p17H8.

Figure 2B:
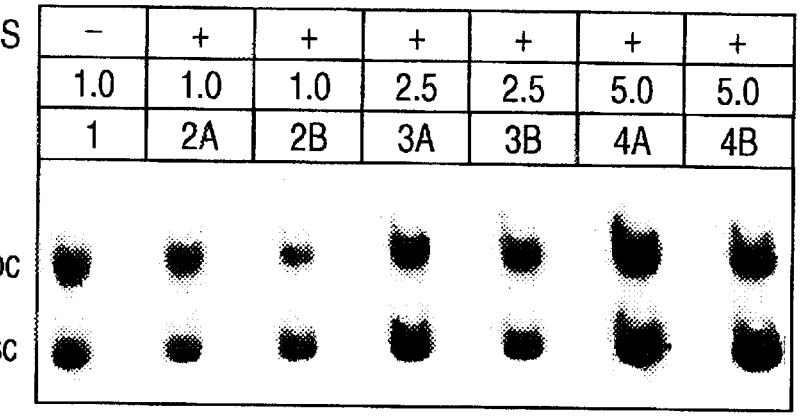
FIG. 2B is an autoradiograph showing rate-dependent third strand binding to sc p17H8 in the presence of ~2,400 unsorted human metaphase chromosomes (1–22, XY). Gel purified $^{32}$P-end-labeled 5'-$Tm^5C$-3' ($0.5\times10^6$ cpm/pmol) and 0.25 µg of 2×CsCl p17H8 were present at a 2:1 oligomer:plasmid molar ratio. 25 µl reactions were carried out in 1×triplex cocktail at pH 6.0 and 23° C. After 1.0, 2.5, and 5.0 hr incubations, the reactions were centrifuged at 3,000 rpm and 4° C. for 30 minutes to pellet the chromosomes. The supernatants were electrophoresed as described above, and film exposure was for 7 hr. Lane 1 contains $^{32}$P-third strand and p17H8, but no chromiosomes. Lanes 2A, 3A, and 4A represent reactions in which chromosomes, $^{32}$P-third strand, and p17H8 were added together, while for lanes 2B, 3B and 4B, chromosomes and $^{32}$P-third strand were preincubated together for 1 hr prior to adding p17H8.

The specificity of third-strand binding to p17H8 was also examined in the presence of increasing amounts of unsorted human metaphase chromosomes (1–22, XY). In these solution binding assays, the stoichiometry of $^{32}$P-end-labeled third strand, 5'-Tm⁵C-3', to p17H8 was 2:1. This permitted any non-specific binding to chromatin DNA, histone and non-histone proteins, or RNA to be detected as decreased plasmid-bound $^{32}$P-third strand. The amount of alpha-satellite target sequence due to chromosome 17 (~1:24) was insufficient to compete against plasmid targets. After 1 hr incubations, plasmid signal intensity was observed to decrease slightly as unsorted chromosomes increased from ~24 to ~2,400. FIG. 2B shows the results of a kinetic experiment that examined this rate-limiting effect on binding to plasmid in the presence of ~2,400 unsorted metaphase chromosomes. It can be seen that sc and oc plasmid-bound $^{32}$P-third-strand signals increase over time, t$_o$=1 hr. Thus, ~2,400 chromosomes, i.e., 6×10$^{11}$ bps of unsorted human chromosomal DNA, did not detectably inhibit or impair the specificity of third-strand binding to p17H8. It merely slowed the kinetics. This result suggested that specificity was achievable for third-strand binding to unique and accessible alpha-satellite target sequences on chromosome 17 in mitotic spreads and nuclei.

Protocol for Third-Strand In Situ Hybridization (TISH)

TISH was performed at pH 6.0 under non-denaturing solution conditions that give quantitative third-strand binding to recombinant DNA molecules. A general protocol is as follows:

Solution Conditions: 1×triplex cocktail for TISH contains 10 mM Bis-Tris-HCl/50 mM KCl/10 mM MgCl$_2$/1 mM DTT/1 mM EDTA/1 μM spermine/2% PEG 8000, pH 6.0 at 23° C. TISH pre-hybridization, post-hybridization, and UVA irradiation buffers are slight variations of this cocktail. The pH of Bis-Tris buffers is temperature sensitive, ΔpH/Δt=−0.014 (pH units/°C.). At the elevated temperatures used for hybridization (45° C.) and post-hybridization washing (51° C.), the pH of TISH buffers is 5.7 and 5.6, respectively.

Pre-hybridization: Room temperature slides containing metaphase spreads and interphase nuclei were dehydrated in successive 2 minute immersions in 70, 80, and 95% ethanol (at 23° C.) incubations. After air-drying, the slides were incubated in TISH pre-hybridization buffer [10 mM Bis- Tris-HCl/50 mM KCl/2.5 mM EDTA/1 mM DTT/pH 6.0] at room temperature for 30 minutes to promote chromosome swelling. For all remaining steps, the slides were never allowed to dry.

Hybridization: TISH hybridization mixtures (final vol. 25 µl) contain 1×triplex cocktail (pH 6.0) supplemented with 1.0–2.5% deionized formamide (BRL, ultrapure), 1.0 ng of blocking RNA (alcohol precipitated, size fractionated total yeast RNA), and ~20 ng of third-strand probe. Hybridization mixtures and slides were pre-heated at 45° C. for 15 minutes in a water bath and humidified chamber, respectively, after which the mixtures were applied to the slides under 22 mm² glass coverslips. Hybridization was performed in the pre-warmed humidified chamber for 2 hours at 45° C.

Post-Hybridization Washing: Slides with coverslips intact were immersed into TISH washing buffer [10 mM Bis-Tris-HCl/75 mM KCl/10 mM MgCl$_2$/1 mM DTT/pH 5.6] at 51° C., agitated to loosen the coverslips, and incubated further for 5 min.

UVA Photochemistry: After removal from the wash buffer, slides were quickly covered with 22 mm² coverslips to which 25 µl of DTT/EDTA-depleted 1×cocktail, pH 6.0, was applied. The slides were then placed in an open petri dish and UVA (320–400 nm) irradiated for 5 minutes (14 watt low pressure mercury arc, model #RPR 3500 Å, The Southern New England Ultraviolet Company, Branford, Conn.). Typical UV irradiance was 1.6 J/cm² per 5 minutes at 320–400 nm. Afterwards, the slides with coverslips intact were placed in 1×PBD, pH 8.0 (phosphate buffer with 0.05% Nonidet P40) at room temperature and agitated to loosen the coverslips. The incubation time in 1×PBD is not critical. Incubation times were generally 2–5 minutes, the longest 1 hour.

Cytochemical Detection: Slides were removed from the 1×PBD, and 60 µl of fluorescein (FITC)-labeled avidin (Oncor, Inc., Gaithersburg, Md.) was applied under a plastic coverslip. After incubation in a pre-warmed humidified chamber at 37° C. for 20 minutes, their plastic coverslips were carefully removed, and the slides then washed three times for 2 minutes each in 1×PBD, pH 8.0, at room temperature. After the final wash, excess fluid was blotted from the slide edges, and 15 µl of propidium iodide (PI)/antifade, pH 8.5, (final PI conc. 0.3 mg/ml) (Oncor, Inc.) was applied under a 22 mm² coverslip. The slides were then incubated for 5 minutes at room temperature.

Epi-fluorescent Microscopy: Fluorescent signals were captured and stored using an Intel pentium powered Oncor Archive 2.0 color imaging system (Oncor, Inc.) consisting of a Zeiss Epi-fluorescent microscope equipped with a 3CCD high resolution color camera controlled by a digital image processor.

Hydrated slides containing non-denatured metaphase spreads and interphase nuclei, isolated by standard cytogenetic methods from human lymphocytes, and a hybrid mouse×human chr. 17 fibroblast cell line (cell line GM10498, Coriell Institute for Medical Research, Camden, N.J.), were incubated with 25 µl of 1×triplex hybridization mixtures containing 20 ng of chromosome 17 α-satellite-specific third strand probe, 5'-Pso-Tm$^5$C-Bio-3'. Optimal parameters for TISH: pre-hybridization hydration (30 minutes at 23° C.), hybridization (2 hours at 45° C.), post-hybridization washing (5 minutes at 51° C.), and UVA (320–400 nm) irradiation (5 minutes) were determined empirically. Post-hybridization washing at elevated temperature and volume effectively promotes dissociation of dual psoralen- and biotin-modified third strands bound to non-target duplex sequences. Subsequent UVA-induced psoralen-DNA photoadduct formation prevents dissociation of target-specific bound third strands containing m$^5$C$^+$ residues at the alkaline pH conditions required for pre-detection wash and FITC-avidin detection. Chromosome 17 centromere-specific fluorescence hybridizations with high signal to noise ratios were obtained in the absence of RNAse A and protease treatment. Moreover, no signal amplification was required.

Figure 3:
FIG. 3 is a standard non-denatured metaphase spread and interphase nucleus prepared for TISH, but "hybridized" with a D17Z1-specific ds probe using a conventional FISH protocol (Oncor, Inc.). Non-denatured spreads and nuclei were hybridized at 37° C. for 1 hr with 5 ng of a denatured 200 bp biotin-11dUTP nick-translated probe (Oncor, Inc.). No fluorescent signals are visible after FITC-avidin-based detection. The chromosomes are stained with PI.

Two approaches were taken to establish that the DNA of non-denatured fixed metaphase spreads and interphase nuclei prepared for TISH are in a duplex state. One exploits fluorescent in situ hybridization (FISH), which requires single-stranded targets. FISH assays performed on non-denatured spreads and nuclei using a standard chromosome 17 D17Z1-specific ~200 bp biotin-labeled probe produced neither centromere-specific nor non-specific fluorescent signals (FIG. 3). The other is based on the general chromosome staining intercalator propidium iodide (PI), which has higher affinity and exhibits greater fluorescence when bound to double-stranded (ds) than to single-stranded (ss) DNA (16). Counterstaining of TISH-assayed non-denatured spreads and nuclei was performed at PI concentrations used for FISH, in which case renaturation in 70% formamide is not quantitative, and should yield a mixture of ds and ss DNA. Non-denatured TISH spreads emitted significantly brighter PI fluorescence than renatured FISH spreads. Together, these observations confirm a duplex state for both chromosome 17 α-satellite and the totality of mitotic chromosomal DNA on slides prepared for TISH.

Chromosome 17-Specific Identification by TISH

Figure 4B:
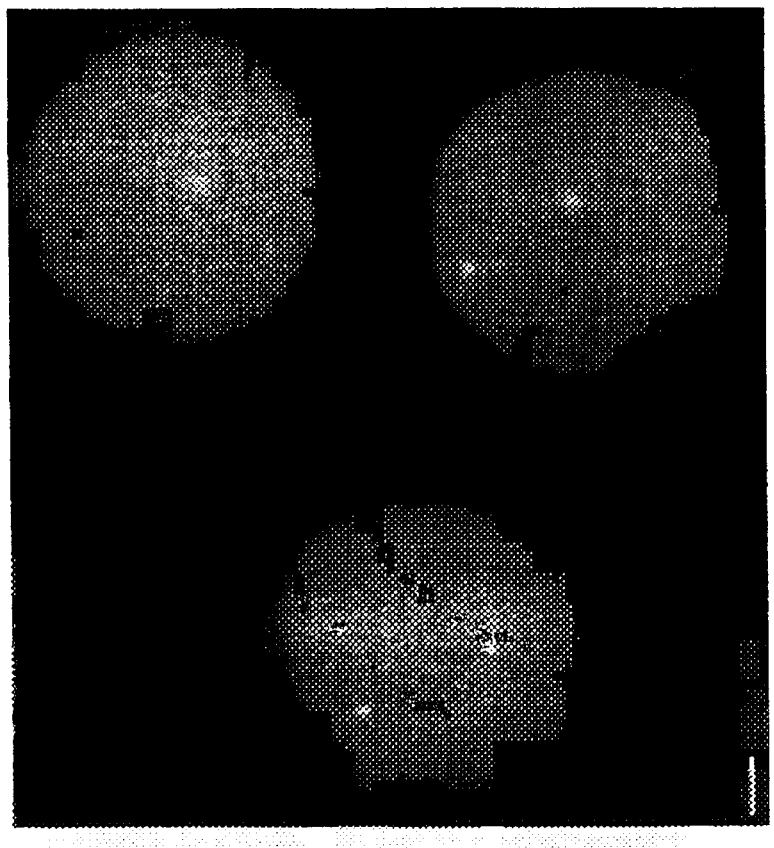
FIGS. 4A and 4B are TISH images of a non-denatured (A) metaphase spread and (B) interphase nuclei hybridized wit the 16-nt chr. 17 -satellite-specific third strand 5'Pso-$Tm^5C$-Bio-3'. FITC-avidin-based detection clearly identifies two centromere-specific fluorescent spots on anatomically homologous metaphase chromosomes that are the expected size for chr.17. Each interphase nucleus shows two fluorescent spots.
Figure 4A:
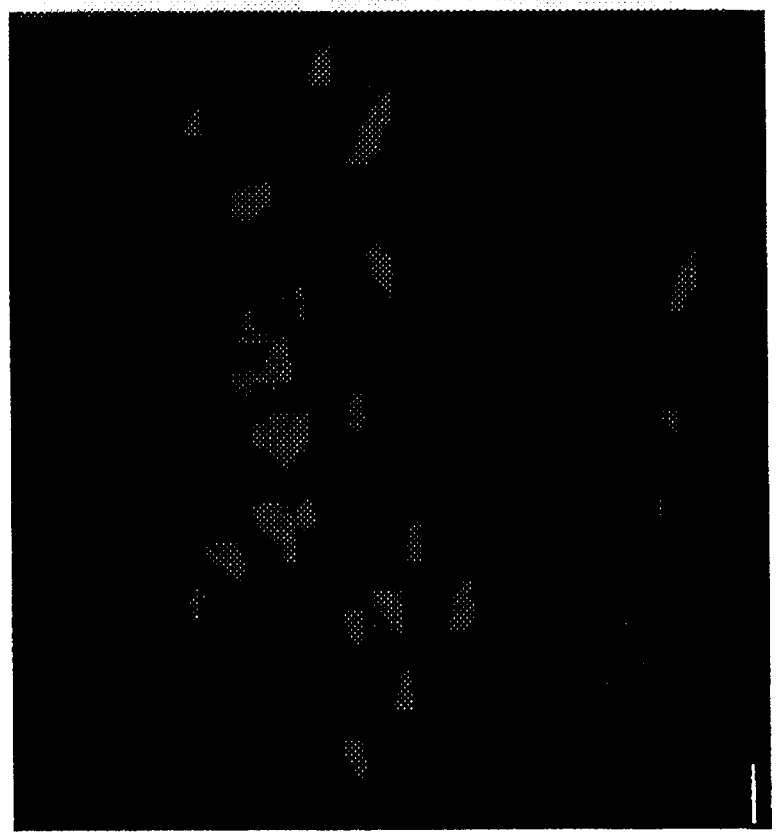
Figure 6B:
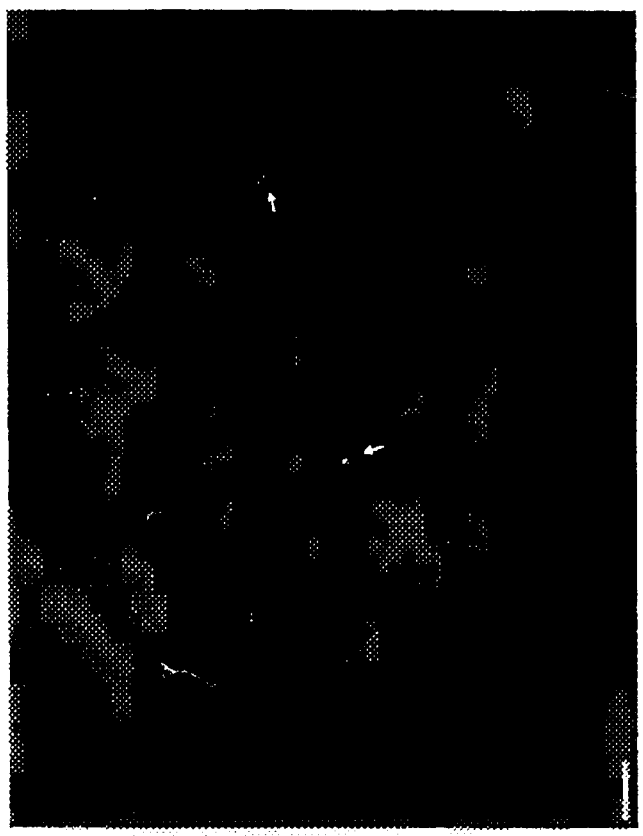
FIGS. 6A–6D are TISH and FISH images of metaphase spreads and interphase nuclei from two individuals differing in their TISH-based chr.17 fluorescent signal patterns. The two haplotypes for third-strand binding, +17 and −17, are shown in two combinations, (A) +17/+17 and (C) +17/−17.
Figure 6A:
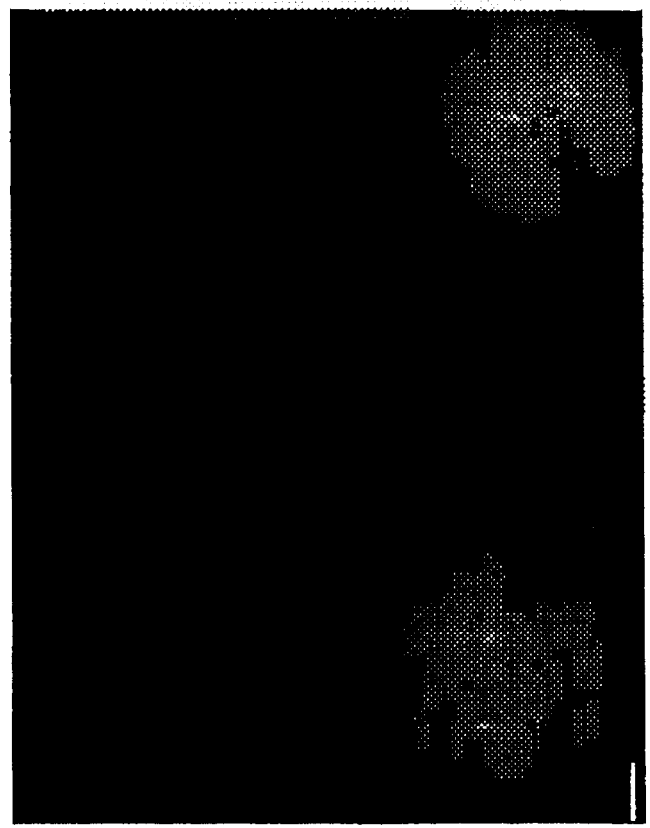
Figure 6D:
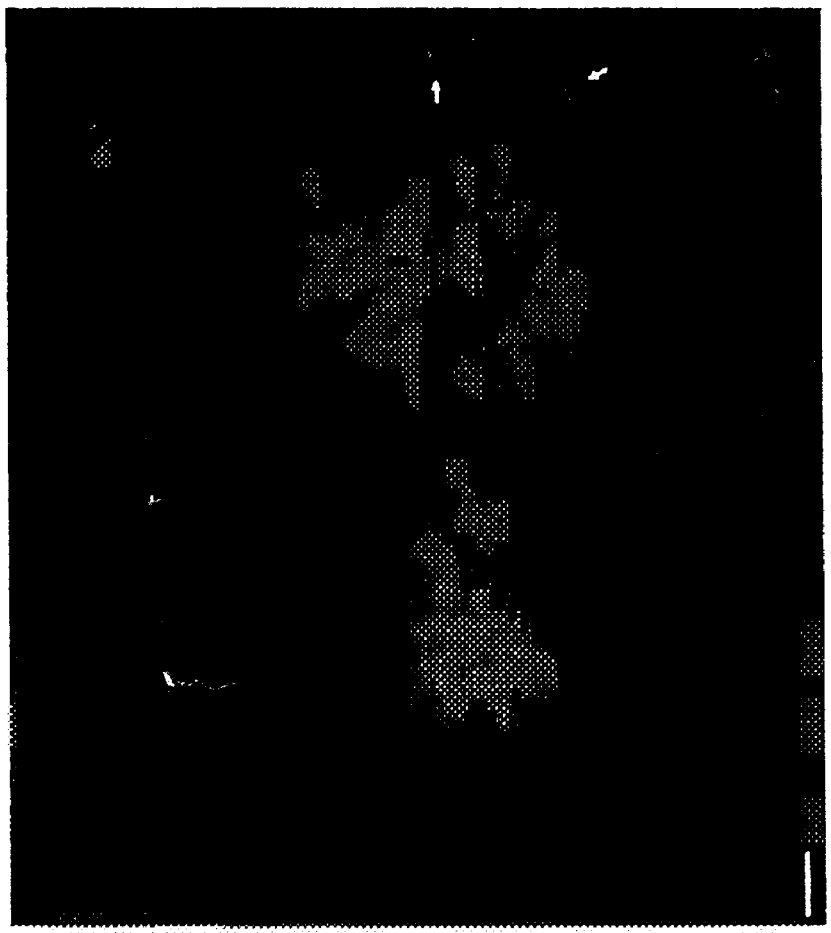
Figure 6C:
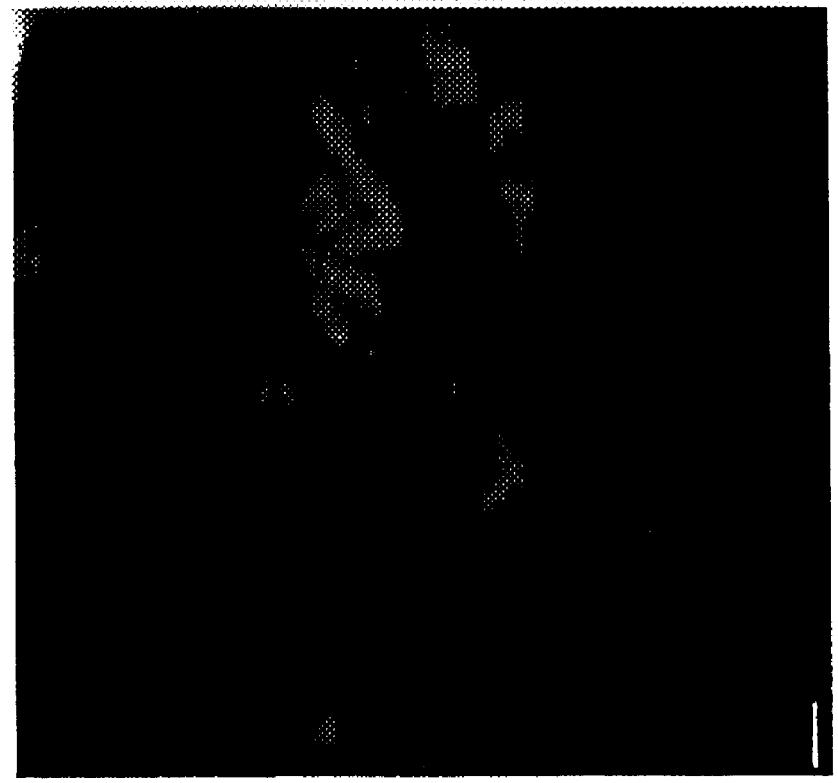

A typical in situ hybridization of 5'-Pso-Tm$^5$C-Bio-3' to a non-denatured fixed metaphase spread and nuclei from a karyotypically normal 46, XY male lymphocyte cell line is shown in FIGS. 4A and B. Detection did not require amplification. The two distinct centromere-specific yellow-green fluorescent spots identifying homologous chromosomes 17 in the metaphase spread and three interphase nuclei were reproduced in ~90% of all spreads and nuclei examined. The other 10% emitted short-lived fluorescent signals that were not capturable due to quenching. More than 250 combined spreads and nuclei per individual examined (5 subjects in total) were scored to ensure statistical significance. Metaphase and prometaphase (not shown) chromosomes 17 were equally labeled. The spatial organization of the fluorescent signals in the three male subject nuclei, one peripherally located, the other more central, was consistent for the bulk of nuclei examined. The spreads and nuclei in FIGS. 4A and B show the empirically determined fluorescence maximum observed after a 2 hour hybridization at 45° C. with 20 ng of probe. Longer hybridizations with 20 ng or more probe did not elicit stronger fluorescent signals, while less time and/or probe produced weaker signals. Under TISH hybridization conditions, saturation of all accessible chromosome 17 α-satellite targets was reproducibly achieved within 2 hours.

The specificity of third-strand probe binding to in situ mitotic chromosomes 17 was additionally confirmed. One approach involved mouse×human somatic cell hybrid metaphase spreads and nuclei containing a single human chromosome 17. Another involved TISH competition assays, in which increasing concentrations of non-covalently modified third strand, 5'-Tm$^5$C-3', were added to compete against 5'-Pso-Tm$^5$C-Bio-3'-specific binding. FIGS. 5A and B show the centromere-specific third strand-based fluorescence of single human metaphase and interphase chromosome 17s in a mouse genomic background. A competition assay (FIG. 5C) demonstrates that when 5'-Pso-Tm⁵C-Bio-3' is competed out, there is no non-specific binding to the remaining human mitotic chromosomes in spreads.

α-Satellite Target Sequence Polymorphism Detected by TISH

Third-strand in situ hybridizations were performed on non-denatured metaphase spreads and nuclei of 5 unrelated individuals, 4 male and 1 female. Three centromere-specific chromosome 17 fluorescent signal patterns were recorded: (+17/+17 homozygotes) when each chromosome 17 homologue was labeled, (+17/-17 heterozygotes) when only one homologue was labeled, and (-17/-17 homozygotes) when neither emitted detectable fluorescence. In contrast, all five individuals yielded detectable +17/+17 FISH-based signals with a ~200 bp biotin-labeled D17Z1 α-satellite probe. FIGS. 6A–D show contrasting TISH and FISH images for two signal patterns. The two variant forms of chromosome 17 (+17 and -17) identified by TISH represent at least two distinct D17Z1 haplotypes.

Inter- and intra-homologue sequence variations identified within the D17Z1 loci of chromosomes 17 can alter effective third-strand target copy number, and so could account for the two variant D17Z1 haplotypes. Inter-homologue sequence variations within α-satellite higher-order repeats of paired chromosomes 17 are characterized by single point mutations in either simple or restriction-enzyme sequences (RFLPs), and as differences in repeat length due to deletions of single or multiple contiguous ~171 bp monomer units (8, 17–19). Data from Warburton and Willard (20) suggest that a partial explanation for the observed variations in third-strand binding to different D17Z1 loci could be target sequence heterogeneity due to a single A→G transition mutation of the second residue (counting 5'→3') of the purine-rich target strand. 5'-Pso-Tm⁵C-Bio-3' third-strand binding affinity would likely be significantly impaired by this mutation at the TISH hybridization temperature of 45° C. since a T:G•C mismatch replaces a canonical T:A•T triplet. In fact, a single T:G•C mismatch in a similar Y:R•Y nearest neighbor environment prohibited third-strand binding at ambient and elevated temperatures (4).

Intra-homologue sequence variation within the megabase -satellite array of individual chr. 17s (18) is characterized by highly amplified localized homogeneous domains containing one distinct type of higher-order repeat unit differing in either sequence or length from flanking repeat units. The existence within different chr. 17 -satellite arrays of such domains containing the altered target sequence (A→G transition) flanked by repeats containing wild-type target sequences could, depending on their respective ratios, further account for the observed variability in third-strand binding. D17Z1 loci having many fewer wild-type target sequences might be expected to exhibit reduced TISH-based fluorescent signals or even none at all at 45° C. In this respect, TISH affords a sensitivity not inherent in FISH.

Third-Strand Target Accessibility

Third-strand probe binding to duplex targets in solution can be described by the following equilibrium:

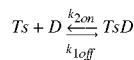

$$Ts + D \underset{k_{1off}}{\overset{k_{2on}}{\rightleftharpoons}} TsD$$

where Ts is the third strand, D is the duplex target, TsD the triplex, and k2on and k1off second-order association and first-order dissociation rate constants. When third strand concentration is in excess to a duplex target, and binding is strong, the reaction is essentially irreversible, and like Watson-Crick reassociation kinetics, pseudo-first-order. Such is the case for third strand titrations to a duplex target of equal length, and to single targets contained within relatively large DNA fragments (≦400 base pairs) or supercoiled plasmids (3). For reactions involving such molecules, the equilibrium lies far to the right.

The TISH experiments described here demonstrate that a 16 residue third strand can bind with specificity to a unique multicopy centromeric target sequence on metaphase and interphase chr. 17s. This result suggests that solvent-exposed areas of non-denatured fixed mitotic chromosomes on slides are accessible to and explorable by third strands. The reproducibility of chr. 17 centromere-specific fluorescent labeling with high signal to noise ratios confirms that third strands can associate with specific chromosomal sequences and dissociate from non-specific ones on slides under solution conditions. This accessibility suggests that in such spreads there are no significant barriers to third strands directed to non--satellite target sequences.

References

1. G. Felsenfeld and A. Rich, *Biochim Biophys Acta* 26, 457 (1957); J. R. Fresco and B. M. Alberts, *Proc. Natl. Acad. Sci. USA.* 46, 311 (1960); J. R. Fresco, in *Informational Macromolecules*, H. J. Vogel, V. Bryson, and J. O. Lampen, Eds. (Academic Press, N.Y., 1963), pp. 121–142; H. E. Moser and P. B. Dervan, *Science* 238, 645 (1987); T. Le Doan, L. Perrouault, D. Praseuth, N. Habhoub, J. L. Decout, N. T. Thoung, J. Lhomme, C. Hélène, *Nucleic Acids Res.* 15, 7749 (1987).
2. A. G. Letai, M. A. Palladino, E. Fromm, V. Rizzo, J. R. Fresco, *Biochemistry* 27, 9108 (1988).
3. L. J. Maher, P. B. Dervan, B. Wold, *Biochemistry* 29, 8820 (1990); P. W. Roberts and D. M. Crothers, *Proc. Natl. Acad. Sci. USA.* 88, 9397 (1991); S. F. Singleton and P. B. Dervan, *Biochemistry* 31, 10995 (1992); S. F. Singleton and P. B. Dervan, *J Am Chem Soc*, 114, 6957 (1992); M. Rougee, B. Faucon, J. L. Mergny, F. Barcelo, C. Giovannangeli, T. Garestier, C. Hélène, *Biochemistry* 31, 9269 (1992).
4. J. A. Fossella, Y. J. Kim, H. Shih, E. G. Richards, J. R. Fresco, *Nucleic Acids Res.* 21, 4511 (1993); K. Yoon, C. A. Hobbs, J. Koch, M. Sardaro, R. Kutny, A. L. Weis, *Proc. Natl. Acad. Sci. USA.* 89, 3840 (1992); G. C. Best and P. B. Dervan, *J Am Chem Soc* 117, 1187 (1995).
5. E. H. Postel, S. J. Flint, D. J. Kessler, M. E,. Hogan, *Proc. Natl. Acad. Sci. USA.* 88, 8227 (1991); W. M. McShan, R. D. Rossen, A. H. Laughter, J. Trial, D. J. Kessler, J. G. Zendegui, M. E. Hogan, F. M. Orson, *J. Biol. Chem.* 267, 5712 (1992); C. Giovannangeli, S. Diviacco, V. Labrousse, S. Gryaznov, P. Charneau, C. Hélène, *Proc. Natl. Acad. Sci. USA.* 94, 79 (1997).
6. S. A. Strobel, L. A. Doucette-Stamm, L. Riba, D. E. Housman, P. B. Dervan, *Science* 254, 1639 (1991).
7. D. Pinkel, T. Straume, J. W. Gray, *Proc. Natl. Acad. Sci. USA.* 83, 2934 (1986); B. J. Trask, *Methods Cell Biol.* 35, 3 (1991).
8. R. Wevrick and H. F. Willard, *Proc. Natl. Acad. Sci. USA.* 86, 9394 (1989).
9. H. F. Willard, G. M. Greig, V. E. Powers, J. S. Waye, *Genomics.* 1, 368 (1987).
10. The Genetics Computer Group (GCG) software from the University of Wisconsin Genetics Computer Group, Inc.
11. J. S. Waye and H. F. Willard, *Mol. and Cell. Biol.* 6, 3156 (1986).

12. H. S. Willard and J. S. Waye, *Trends Genet.* 3, 192 (1987).
13. J. S. Waye and H. F. Willard, *Nucleic Acids Res.* 14, 6915 (1986).
14. T. J. Povsic and P. B. Dervan, J. Am. Chem. Soc. 111, 3059 (1989); G. E. Plum, Y. W. Park, S. F. Singleton, P. B. Dervan, K. J. Breslauer, *Proc. Natl. Acad. Sci. USA.* 87, 9236 (1990); L. E. Xodo, G. Manzini, F. Quadrifoglio, G. A. van der Marel, J. H. van Boom, *Nucleic Acids Res.* 19, 5625 (1991).
15. M. D. Johnson and J. R. Fresco, in preparation.
16. E. J. Gabbay and W. D. Wilson, *Methods Cell Biol.* 18, 351 (1978).
17. H. F. Willard, J. S. Waye, M. H. Skolnick, C. E. Schwartz, V. E. Powers, S. B. England, *Proc. Natl. Acad. Sci. USA.* 83, 5611 (1986).
18. P. E. Warburton and H. F. Willard, *J. Mol. Biol.* 216, 3 (1990).
19. P. E. Warburton and H. F. Willard, *J. Mol. Evol.* 41, 1006 (1995).
20. P. E. Warburton and H. F. Willard, *Nucleic Acids Res.* 20, 6033 (1992).

What is claimed is:

1. A method for detecting in situ the presence of a target sequence in a substantially double-stranded nucleic acid segment, which comprises:

a) contacting in situ under conditions suitable for third strand hybridization a substantially double-stranded nucleic acid segment with a detectable third strand, said third strand being capable of hybridizing to at least a portion of the target sequence to form a triple-stranded structure, if said target sequence is present; and b) detecting whether hybridization between the third strand and the target duplex sequence has occurred to thereby detect the presence of the target sequence.

2. The method of claim 1, wherein the third strand comprises DNA or RNA.

3. The method of claim 1, wherein the third strand comprises an unnatural heterocycle base substitute, a base analog, an unnatural backbone, or a substituent which strengthens binding of the third strand to the target sequence.

4. The method of claim 1, wherein the target sequence is within a human chromosome α-satellite region, other satellite regions, or non-satellite heterochromatin or euchromatin regions.

5. The method of claim 4, wherein the target sequence is within a human chromosome α-satellite region.

6. The method of claim 5, wherein the target sequence is within the human chromosome 17 α-satellite region.

7. The method of claim 6, wherein the third strand comprises at least 10 contiguous bases contained within SEQ ID NO:2.

8. The method of claim 6, wherein the third strand comprises the sequence of SEQ ID NO:2.

9. The method of claim 1, wherein the hybridization takes place in a metaphase spread.

10. The method of claim 1, wherein the hybridization takes place in an interphase nucleus.

11. The method of claim 1, wherein the third strand is labeled with a moiety capable of being directly or indirectly detected.

12. The method of claim 11, wherein the third strand is labeled with a compound selected from the group consisting of biotin, fluorescein, digoxigenin, rhodamine and phenyloxazolone.

13. The method of claim 1, wherein the detection step takes place without a prior amplification step.

14. The method of claim 1, wherein the detection step takes place subsequent to an amplification step.

15. The method of claim 1, wherein the third strand is designed to allow detection of extra or missing chromosomes, extra or missing portions of a chromosome, or chromosomal rearrangements.

16. The method of claim 15, wherein the third strand is designed to allow detection of aneuploidy.

17. The method of claim 16, wherein the aneuploidy is an extra or missing human chromosome 17.

18. The method of claim 16, wherein the aneuploidy is an extra or missing human chromosome 21.

19. The method of claim 1, wherein the target sequence contains any one of SEQ ID NO:3 through SEQ ID NO:75.

20. The method of claim 1, wherein the method is diagnostic of a genetic disorder.

21. The method of claim 1, wherein the method is used to screen individuals at risk for developing a disease.

22. The method of claim 1, wherein the method is diagnostic of an infectious disease.

23. The method of claim 1, wherein the target sequence is within a chromosomal region of a eukaryotic species or the double-stranded stage of a virus.

24. The method of claim 1, wherein the third strand comprises a moiety capable of enhancing the binding of said third strand to-said target sequence.

25. The method of claim 24, wherein said moiety is a DNA binding agent, a DNA cross-linking agent, or a DNA intercalating agent.

26. The method of claim 25, wherein the moiety is psoralen, and wherein the method further comprises the step of irradiating the triple-stranded structure with UV light so as to covalently affix the third strand to the target sequence.

* * * * *

SEQUENCE LISTING

```
<160> NUMBER OF SEQ ID NOS: 77

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:  purine
      rich DNA target strand

<400> SEQUENCE: 1
aaaaagaaga cagaag                                                       16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:
      homopyrimidine third strand DNA probe

<400> SEQUENCE: 2
tttttcttct ttcttc                                                       16

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 3
agtaaaggaa agaa                                                         14

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:  Target
      sequences

<400> SEQUENCE: 4
tatttccttt tctcgctt                                                     18

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:  Target
      sequences
```

-continued

```
<400> SEQUENCE: 5
gaatgaaaag gaaag                                                15

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Target
      sequences

<400> SEQUENCE: 6
tttccttttc tcgcttt                                              17

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 7
aaaggtagaa aaggaaata                                            19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 8
aaaggcagaa aaggaaata                                            19

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 9
cttttctttt tcattc                                               16

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 10 cctttcttttt gagagagcag                                          20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Target
      sequences
```

<400> SEQUENCE: 11
gaaaaaggaa atatcttccc ct                                              22

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:  Target
      sequences

<400> SEQUENCE: 12
tttacccctt tcttttc                                                    17

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 13
gatagaaaag gaaa                                                       14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 14
ggtagaaaag gaaa                                                       14

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:  Target
      sequences

<400> SEQUENCE: 15
ctttccttta gaaaacagca gag                                             23

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 16
ggaaaaaaag gata                                                       14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 17
ctttctcctt actt                                                          14

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Target
      sequences

<400> SEQUENCE: 18
gaaaagggag gtttcactct tt                                                 22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Target
      sequences

<400> SEQUENCE: 19
ctttctctac caaagaaag g                                                   21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 20
ggtgaaaatg gaaaggaaa                                                     20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 21
gaggcaaatg gagaaaaag                                                     19

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 22
tcctttcttt tcattc                                                        16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 23

```
acagaggaaa aggaaa                                                   16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:  Target
      sequences

<400> SEQUENCE: 24
atggaggaaa aggaaa                                                   16

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:  Target
      sequences

<400> SEQUENCE: 25
agagatgaac ctttcttttt                                               20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:  Target
      sequences

<400> SEQUENCE: 26
acggggagaa aggaaata                                                 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:  Target
      sequences

<400> SEQUENCE: 27
atggagagaa aggaaata                                                 18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:  Target
      sequences

<400> SEQUENCE: 28
agagggagca gaggtgaaa                                                19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:  Target
      sequences

<400> SEQUENCE: 29 tttctcctttc ctcttcat                                                18
```

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 30
ttccaccttt cttttc                                                  16

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Target
      sequences

<400> SEQUENCE: 31
cctttcttga gagagagcag a                                            21

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 32
tttcaccttt ctcttc                                                  16

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Target
      sequences

<400> SEQUENCE: 33 ccttcctttp gagagagcag a                                            21

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 34
aaaggtagaa aaggaaaca                                               19

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 35
gaagagaaag gtgaaa                                                  16

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 36 cctttcttttt gatggaggag                                              20

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Target
      sequences

<400> SEQUENCE: 37
ctctctctaa agaaagg                                                  17

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 38
aaaggtagaa aaggaaata                                                19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 39
cctttctttt gatgaaggag                                               20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 40
ggaaacggga tttcttcct                                                19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 41
cctttctttt gatgaaggag                                               20

```
<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Target
      sequences

<400> SEQUENCE: 42
ggtgaaaaag ggaa                                                      14

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 43
gaaaaaggga atgtcttccc                                                20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Target
      sequences

<400> SEQUENCE: 44
agagtggaac ctctctcttt t                                              21

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Target
      sequences

<400> SEQUENCE: 45
ggtgagaaag gaaa                                                      14

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 46
agaggtggat ctttctttt                                                 19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Target
      sequences

<400> SEQUENCE: 47
aaagggaata tcttcccct                                                 19

<210> SEQ ID NO 48
```

```
<211> LENGTH: 14
<212> TYPE: DNA
<213> ORGANISM: Artificial Sequence
<220> FEATURE:
<223> OTHER INFORMATION: Description of Artificial Sequence: Target
      sequences

<400> SEQUENCE: 48
ggtgaaaagg gaaa                                                           14

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 49
gaaaagggaa atatcttctc                                                     20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Target
      sequences

<400> SEQUENCE: 50
aacagagaag aaccttcctt tt                                                  22

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 51
tttcaccttt cttttc                                                         16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 52
agaaagaaga cagaag                                                         16

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 53
aaaaagaaga cagaag                                                         16

<210> SEQ ID NO 54
<211> LENGTH: 15
```

```
<212> TYPE: DNA
<213> ORGANISM: Artificial Sequence
<220> FEATURE:
<223> OTHER INFORMATION: Description of Artificial Sequence: Target
      sequences

<400> SEQUENCE: 54
ttttttttcc tctct                                                          15

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Target
      sequences

<400> SEQUENCE: 55
ctttcctttc gagagaag                                                       18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Target
      sequences

<400> SEQUENCE: 56
ttttcctttc gagagagaag                                                     20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Target
      sequences

<400> SEQUENCE: 57
ggaaaaggaa ttatctttcc c                                                   21

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 58
aaggtgaaaa aggaaa                                                         16

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: Target
      sequences

<400> SEQUENCE: 59
atggagagaa aggaaa                                                         16

<210> SEQ ID NO 60
<211> LENGTH: 15
<212> TYPE: DNA
```

```
<213> ORGANISM: Artificial Sequence
<220> FEATURE:
<223> OTHER INFORMATION: Description of Artificial Sequence:  Target
      sequences

<400> SEQUENCE: 60
aaggtgaaaa agaaa                                                       15

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence:  Target
      sequences

<400> SEQUENCE: 61
aaaggagtag aacctttctt ttc                                              23

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 62
ggtgaaaaag gaga                                                        14

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 63
ggtgaaaaag gaaa                                                        14

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:  Target
      sequences

<400> SEQUENCE: 64 gaaaaggaa atatcttccc                                                   20

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 65
ggtggagaag gaaa                                                        14

<210> SEQ ID NO 66
<211> LENGTH: 19
<212> TYPE: DNA
<213> ORGANISM: Artificial Sequence
```

```
<220> FEATURE:
<223> OTHER INFORMATION: Description of Artificial Sequence:  Target
      sequences

<400> SEQUENCE: 66
ggaaaagaat tatcttctc                                                    19

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 67
ggtggaaaag gaaa                                                         14

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence:  Target
      sequences

<400> SEQUENCE: 68
agtggaaaag gaaa                                                         14

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence:  Target
      sequences

<400> SEQUENCE: 69
ttccctttca gagagcag                                                     18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence:  Target
      sequences

<400> SEQUENCE: 70
aaaggaaata tcttcccct                                                    19

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence:  Target
      sequences

<400> SEQUENCE: 71
acagaaagac gagagagaag ca                                                22

<210> SEQ ID NO 72
<211> LENGTH: 17
<212> TYPE: DNA
<213> ORGANISM: Artificial Sequence
<220> FEATURE:
```

```
<223> OTHER INFORMATION: Description of Artificial Sequence:  Target
      sequences

<400> SEQUENCE: 72
cctttTccTT TaTcTTc                                                        17

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:  Target
      sequences

<400> SEQUENCE: 73
ggaaaaggaa atatcttctc c                                                   21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence:  Target
      sequences

<400> SEQUENCE: 74
ggaagatggt ggaaaaggaa a                                                   21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:  Target
      sequences

<400> SEQUENCE: 75
ggaaaaggaa gtatcttcct                                                     20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:  Target
      sequences

<400> SEQUENCE: 76
ctataaaaag aagacagaag                                                     20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:  target
      sequence

<400> SEQUENCE: 77
gatatttttc ttctgtcttc                                                     20
```